US00RE39815E

(19) United States
(12) Reissued Patent
Gage et al.

(10) Patent Number: US RE39,815 E
(45) Date of Reissued Patent: Sep. 4, 2007

(54) METHOD FOR DETERMINING ION CHANNEL ACTIVITY OF A SUBSTANCE

(75) Inventors: Peter William Gage, deceased, late of Queanbeyan (AU); by Angela Fay Dulhunty, legal representative, Queanbeyan (AU); Graeme Barry Cox, Bawley Point (AU); Gary Dinneen Ewart, Hackett (AU)

(73) Assignee: The Australian National University, Acton (AU)

(21) Appl. No.: 10/800,361

(22) PCT Filed: Sep. 26, 1997

(86) PCT No.: PCT/AU97/00638

§ 371 (c)(1),
(2), (4) Date: Jun. 30, 1999

(87) PCT Pub. No.: WO98/13514

PCT Pub. Date: Apr. 2, 1998

Related U.S. Patent Documents

Reissue of:
(64) Patent No.: 6,355,413
Issued: Mar. 12, 2002
Appl. No.: 09/269,278
Filed: Jun. 30, 1999

(30) Foreign Application Priority Data

Sep. 27, 1996 (AU) ..... PO2581

(51) Int. Cl.
*C12Q 3/00* (2006.01)
*C12Q 1/70* (2006.01)
*C12P 1/00* (2006.01)
*C12N 11/00* (2006.01)
*C12N 5/00* (2006.01)

(52) U.S. Cl. ..... 435/5; 435/3; 435/5; 435/41; 435/69.3; 435/325

(58) Field of Classification Search ..... 435/4, 435/3, 5, 7.1, 7.2, 41, 69.3, 174, 325
See application file for complete search history.

(56) References Cited

U.S. PATENT DOCUMENTS 4,681,852 A * 7/1987 Tribe ..... 435/108
5,846,757 A * 12/1998 Harpold et al. ..... 435/29

FOREIGN PATENT DOCUMENTS

AU 34602/89 11/1989

OTHER PUBLICATIONS

Schubert et al. American Society for Microbiology. 1995, p. 63.*
Derwent Abstract Accession No. 92–175825/22, Class B04, D16, DD 297186, A (University Berlin Humboldt), Jan. 2, 1992.
Piller et al., "Vpr protein of human immunodeficiency virus type 1 froms cation–selective channels in planar lipid bilayers, PNAC"; vol. 93, pp. 111–115.
Yamato et al., "Site specific alteration of arginine 376 the unique postively charged . . . "; J. Biol. Chem; vol. 269, No. 8, pp. 5720–5724.
Schubert et al., American Society for Microbiology, 1995, p. 63.
Wolfgan Schreibmayer et al., "Mechanism of modulation of single sodium channels from skeletal muscle by the $\beta_1$ subunit from rat brain", 1994, European Journal of Physiology, Pflügers Arch, vol. 426, No. 3–4, pp. 360–362.

* cited by examiner

*Primary Examiner*—Jeffrey Stucker
*Assistant Examiner*—Louise Humphrey
(74) *Attorney, Agent, or Firm*—Fish & Richardson P.C.

(57) ABSTRACT

A method for determining the ion channel activity of a substance comprises the steps of (i) expressing the substance as a heterologous protein in a host cell, and (ii) determining changes in permeability of the plasma membrane of the host cell induced by expression of the heterologous protein. A screening method for determining ion channel modulating activity of a test substance is also disclosed.

11 Claims, 7 Drawing Sheets

Figure 2A:
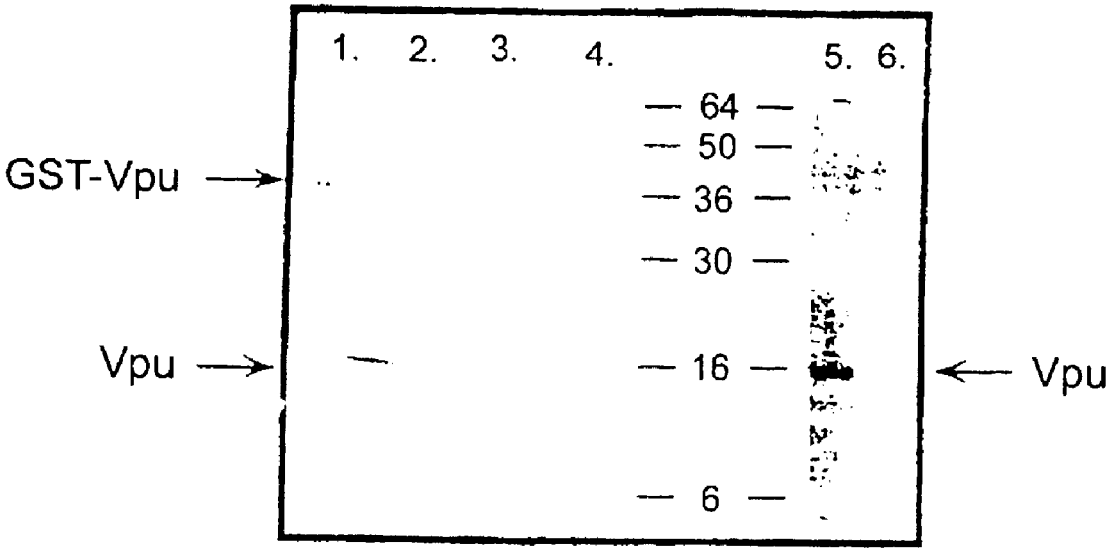

10 20 30 40 50 60 70 80
MQPIPIVAIVALVVAIIIAIVVWSIVIIEYRKILRQRKIDRLIDRLIERAEDSGNESEGEISALVEMGVEMGHHAPWDVD
FIG. 1A
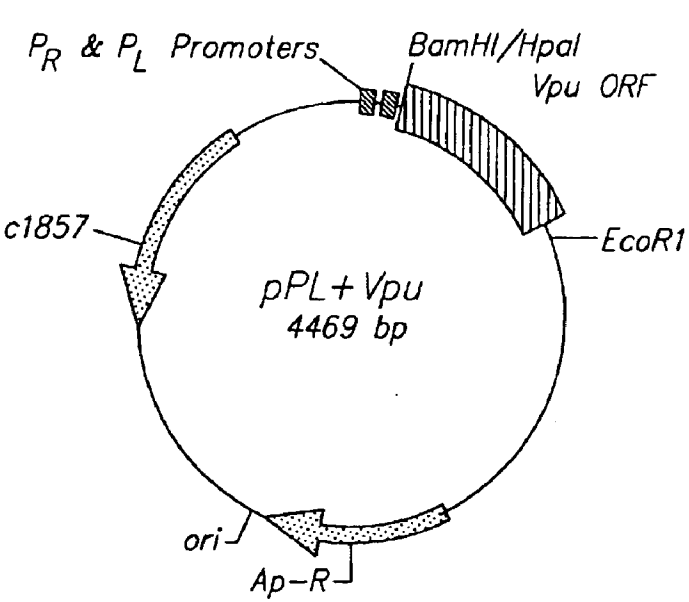
FIG. 1C
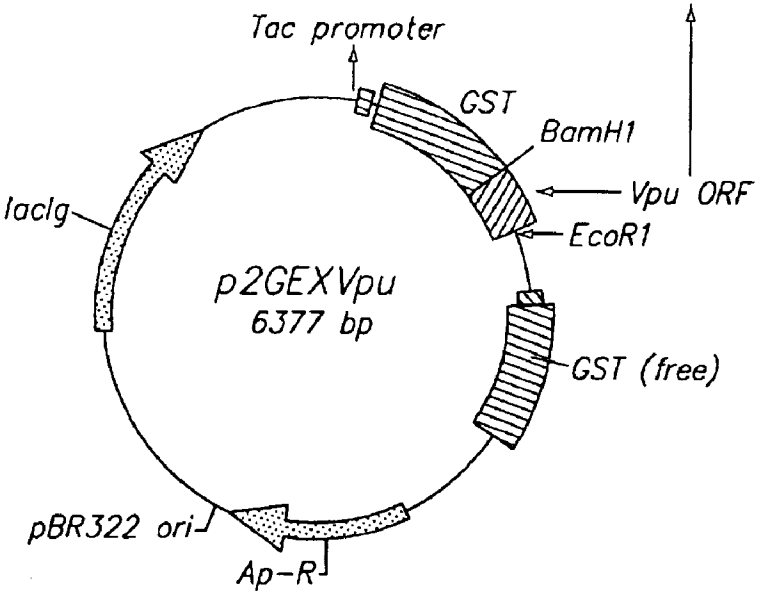
FIG. 1B Cells expressing wild type Vpu Cells containing control plasmid (no Vpu)

Cells expressing wild type Vpu

Cells containing control plasmid (no Vpu)

METHOD FOR DETERMINING ION CHANNEL ACTIVITY OF A SUBSTANCE

Matter enclosed in heavy brackets [ ] appears in the original patent but forms no part of this reissue specification; matter printed in italics indicates the additions made by reissue.

FIELD OF THE INVENTION

This invention relates to a method for determining ion channel activity of substances such as peptides, polypeptides and proteins and to a method for screening potential therapeutic substances for their ability to modulate ion channel function.

BACKGROUND OF THE INVENTION

Biological cells are encapsulated in a membrane made of a double layer of lipids separating the intracellular contents from the outside. The lipid bilayer "sandwich" has a hydrophobic interior that prevents movement of charged particles such as ions across it. However, there are protein macromolecules that penetrate the membrane and act as portholes to allow ions to pass between the inside and outside of a cell. These structures that allow rapid movements of ions (many millions per second) across a cell membrane, with no need for an immediate energy input, are called "ion channels". The forces that influence the movement of ions through a channel are electrical and chemical. The electrical force is the electrical potential across the membrane, the chemical force is the difference in concentration of an ion on the two sides of the membrane: the combination of the two is the electrochemical gradient for an ion. If the electrochemical gradient for an ion is not zero, ions will flow through a channel when it opens (as long as the channel lets them through).

There are many varieties of ion channels that differ in their selectively, methods of gating, conductance and kinetic properties. Channels can be selective for sodium ions, or for potassium ions, or for calcium ions, or for chloride ions, or form protons etc and are classified according to the ions that pass through them most freely. For example, sodium channels are more permeable to sodium than to any other cations or anions. Channels are also classified according to the way in which they are turned on or gated. For example, voltage-activated channels open or close in response to changes in membrane potential. Ligand-gated channels are turned io when ligands such as neurotranmitters or hormones bind to their surface. Proteins to which ligands bind are commonly called receptors and many receptors are part of the same macromolecule that forms the ion channel. However, some channels are indirectly linked to receptors by second messenger systems and the channel is then separate from the receptor. Channels can also have very different conductances. Conductance, the reciprocal of resistance, is a measure of the ease with which ions pass through a channel and is given by the ratio of the current to the driving force. The conductance of different channels can range from picosiemens to hundreds of picosiemens (corresponding to resistances of $10^9$ to $10^{12}$ ohms). Finally, channels can have very different "duty cycles". Some are open most of the time while others open infrequently. Some flicker rapidly between open and closed states while others do not. Changes in the environment of channels (e.g the presence of drugs) can change these characteristics. Indeed it is becoming clear that many drugs exert their effects on cells and organs by binding to surface receptors and influencing channel behaviour.

The function of all cells in an animal or other organism depends on the ion channels formed by membrane proteins which provide a pathway for movement of ions between compartments in a cell and between the interior and exterior of cells. These movements of ions are essential for normal cell function, and all biological cells (including bacteria and even enveloped viruses such as the influenza and HIV viruses) contain ion channels. Ion channels are fundamental to cellular functions such as transmission of signals in nervous systems, cell division, production of antibodies by lymphocytes, replication of virus particles within cells and secretion of fluid and electrolytes.

A wide variety of diseases such as cystic fibrosis, muscular dystrophies, stroke, epilepsy and cardiac arrhythmias are related to disorders of ion channel function. In addition, it has recently been discovered that some viruses have proteins that form ion channels that are needed in the normal life-cycle of the virus. For example, there is now good evidence that a protein (M2) in influenza A virus forms an ion channel that is necessary for virus replication, and drugs such as amantadine that block this channel inhibit replication of the influenza A virus. Amantadine (1-aminoadamantane hydrochloride) and its analogue rimantidine have been found empirically to be effective in the prophylaxis and treatment of influenza caused by the influenza A virus. These drugs, at the therapeutic concentrations, inhibit replication of the influenza A virus both in vitro and in vivo. However, they can become ineffective because of the development of resistant strains of the virus and this reduces their value as therapeutic agents.

Other drugs which work by modulating ion channel function include calcium channel blockers which are used as anti-anginal and antihypertensive agents, barbiturates which cause sleep and inhibit epileptic seizures by increasing movements of chloride ions across receptors activated by gamma-amininobutyric acid (GABA), and benzodiazepines which relieve anxiety and produce anaesthesia by increasing GABA receptor activity.

In the past, the discovery of drugs which block ion channels has been largely serendipitous. Drugs that have been discovered in this way include general anaesthetics such as ether and halothane, the barbiturates and benzodiazepines. Thus, ether was originally used like alcohol at parties, and the reversible anaesthetic effect of halothane was discovered during leakage of refrigerant from a compressor. Similarly, the discovery of the antiarryhthmic action of quinidine followed use of quinine as an antimalarial drug.

Realisation that ion channels could prove to be an important site of drug action has lead to a search for effective ways of screening the activity of potential therapeutic substances that affect ion channel activity. Although electrophysiological techniques can be used to detect current flow when ions move across channels, the methods are too tedious and time-consuming for routine screening of ion channel activity.

Vpu is a small phosphorylated integral membrane protein encoded by the HIV-1 genome which associates with the Golgi and endoplasmic reticulum membranes in infected cells, but has not been detected in the plasma membrane nor in the viral envelope. The protein is 80–82 amino acids long depending on the viral isolate, with an N-terminal transmembrane anchor and a hydrophilic cytoplasmic C-terminal domain. The C-terminal domain contains a 12 amino-acid sequence that is conserved in all isolates and contains two serine residues that are phosphorylated. Using standard techniques associated with reconstitution of the purified HIV-1 Vpu protein in planar lipid bilayers, it has been shown that the Vpu protein forms cation selective ion channels in phospholipid bilayers (8). Further work is now directed to finding drugs that block these channels, and testing them as potential anti-HIV-1 therapeutic agents. While screening for such drugs is possible using the above mentioned planar lipid bilayer method, this method has the disadvantage of requiring large quantities of highly purified Vpu protein and is limited in that only one compound can be tested per bilayer, making it a relatively slow and inefficient screening assay.

Because of these disadvantages, there is a need for an ion channel assay system that can be used both to detect the ion channel activity of biologically important peptides and proteins, and to screen the effectiveness of potential therapeutic substances that might interact with ion channels and modulate ion channel function.

Some organisms such as bacteria accumulate amino acids and other substances by using the energy of a cation concentration gradient. If a substance such as a peptide, polypeptide or protein that forms a channel is inserted in the cell membrane and dissipates the gradient, the organism can no longer accumulate essential substances and growth is inhibited. This growth inhibition can be detected directly. Thus, the activity of potential therapeutic substances that might influence the function of a channel can be quickly screened by examining their effects on growth of an organism containing the channel-forming peptide, polypeptide or protein.

SUMMARY OF THE INVENTION

In one aspect, the present invention provides a method for determining ion channel activity of a substance which is a peptide, polypeptide, protein or the like, which comprises the steps of:

(i) expressing said substance as a heterologous protein in a host cell; and (ii) determining changes in permeability of the plasma membrane of said host cell induced by expression of said heterologous protein.

Preferably, the determination of changes in the permeability of the plasma membrane of the host cell is carried out by detecting changes in the permeability of the plasma membrane to small metabolite molecules, for example proline or adenine.

In accordance with this aspect of the invention, if the test substance is expressed as a heterologous protein having ion channel activity, expression of the heterologous protein in the plasma membrane of the host cell will alter the ability of the cell to maintain concentration gradients of small metabolite molecules such as proline or adenine whose transport into the cell is energised by the ions which are permeable to the expressed channel. As a result, a net movement or leakage of the metabolite molecules out of the cell will occur, and such leakage of the metabolite molecules can then be detected by a suitable method. Preferred methods for detecting leakage of the metabolite molecules from the cell are described below.

In a further aspect, the present invention provides a screening method for determining ion channel modulating activity of a test substance, which comprises the steps of:

(i) expressing a substance having ion channel activity as a heterologous protein in a host cell;

(ii) contacting said host cell with the test substance; and (iii) determining changes in ion channel activity of said heterologous protein induced by the test substance.

Preferably, in this aspect of the invention, changes in ion channel activity of the heterologous protein induced by the test substance are determined by detecting the effect of the test substance on changes in permeability of the plasma membrane of the host cell induced by expression of the heterologous protein in the cell; in particular, by detecting the effect of the test substance on changes in the permeability of the plasma membrane of the host cell to small metabolite molecules such as proline, adenine or the like.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

In a preferred embodiment, the assay method of the present invention measures the alteration of the permeability to small metabolite molecules (proline or adenine, for example) of the plasma membrane of living host cells (E. coli, for example) induced by the expression of heterologous cation (sodium, for example) channel proteins (Vpu, for example) in the host cells. Although the following detailed description is directed specifically to Vpu ion channels, it will be understood that the concept of the assay is generally applicable to any ion channel protein that can be actively expressed in a host cell such as E. coli.

The plasma membrane of a cell generally contains proteins whose function is the uptake of metabolite molecules into the cell. In a subset of these proteins, the energy to drive the uptake reaction is derived from transmembrane concentration gradients of various ions (eg Na+, H+) such that the movement across the membrane and into the cell of the metabolite to be taken up is tightly coupled to the movement across the membrane of an ion moving down its concentration gradient. If a heterologous channel forming protein is present in the membrane of the cells and causes the dissipation of the concentration gradient of the ion driving the uptake of a metabolite, then a net movement of the metabolite out of the cell should occur—particularly in the case where the metabolite can be derived biosynthetially by the cell. Leakage of the metabolite from cells expressing the ion channel can be detected, for example : (i) by either the ability of the leaked metabolite to support the growth of a second type of cell that has an auxotrophic requirement of the leaked metabolite; or (ii) in the case where biosynthesis of the metabolite is rate limiting to growth, by the failure of cells expressing the heterologous channel forming protein to thrive in the absence of externally supplied metabolite.

As a specific example of the first detection method, the E. coli proline transporter is driven by the co-transport into the cell of sodium ions with proline. Cross-feeding between a strain of E. coli expressing the HIV-1 Vpu protein—which consequently leaks proline due to dissipation of the sodium gradient—and a second strain of E. coli that cannot synthesise proline but instead must take it up from the external medium has been demonstrated. Such experiments are performed in proline deficient medium so that the only possible source of proline is via biosynthesis in the Vpu-expressing strain.

As a specific example of the second detection method, the expression of Vpu in E. coli strain XL-1 Blue at 37° C. makes cell growth dependent on externally supplied adenine. The same strain in the absence of Vpu expression grows well when adenine is absent from the growth media.

The in vivo assay of ion channel function described above also has the advantages of speed and efficiency over the planar lipid bilayer assay (8) as a method for screening potential therapeutic substances that might block, inhibit or otherwise modulate the ion channel function as many (hundreds) such substances can be screened in a single experiment. Thus the present invention also provides a method for rapidly screening compounds for their ability to block, inhibit or otherwise modulate the function of ion channel proteins expressed in living cells.

As previously described, the assay method relies on expression of the ion channel forming proteins in the plasma membrane of the cells, altering the ability of the cell to maintain concentration gradients of the metabolites whose transport into the cells is energised by the ions which are permeable to the expressed channel. Leakage of the metabolite from the cell is preferably detected by one of two methods:

(i) cross-feeding of a second strain of cells which are auxotrophic for the leaked metabolite; or (ii) failure to thrive of the cells expressing the ion channel in the absence of the leaking metabolite supplied in the external medium.

Preferably, the expression system involves the expression of ion channel proteins in E. coli from their corresponding genes (preferably cDNA segments) cloned into E. coli plasmid expression vectors. Such vector construction and expression in E. coli uses the standard methods associated with E. coli genetics and molecular biology, described by way of example, by Sambrook et al.(9).

One preferred embodiment of the method of the present invention arises from the observation of cross-feeding between two cell lines—preferably bacterial cells—induced in response to ion channel activity of the expressed foreign gene(s). In the specific case where E. coli cells are being used and a sodium channel is being expressed (for example as detailed further below), the leakage of proline (a metabolite whose transport into cells is energised by the sodium gradient) from the channel-expressing cells can be detected by cross-feeding of a second strain of E. coli that is auxotrophic for proline (i.e. unable to synthesis proline). Control experiments to establish that the expressed channel is not inducing a non-specific leak of all small molecules through the cell membrane would be set up identically to detect methionine leakage. The E. coli methionine transporter is energised by ATP hydrolysis and therefore the absence of a sodium gradient should not induce leakage of methionine out of the cells.

As described above, the present invention also extends to a method for screening potential therapeutic substances that may act as ion channel inhibitors. This screening method is a simple extension of the assay method described above, which in one preferred embodiment involves setting up the cross-feeding assay in the same way as previously described, with the addition of the various substances to be tested to the cells expressing the ion channel protein. Substances which block or inhibit the ion channel activity would prevent dissipation of the permanent ion gradient, and would thereby not induce leakage of metabolites. Control experiments could be performed simultaneously to ensure the substances being tested do not affect the normal growth of E. coli. If such substances are found, they would be excluded from screening by the cross-feeding assay.

Further features of the present invention are more fully described in the following Example(s). It is to be understood, however, that this detailed description is included solely for the purposes of exemplifying the present invention, and should not be understood in any way as a restriction on the broad description of the invention as set out above.

In the accompanying drawings:

FIGS. 1A–1C Plasmids used for the expression of Vpu in E. coli. A. The amino acid sequence encoded by the Vpu open reading frame (ORF) generated by PCR from an HIV-1 strain HXB2 cDNA clone (SEQ ID No.1), as described in Example 1. The Vpu ORF was cloned in-frame at the 3' end of the GST gene in p2GEX to generate p2GEXVpu (B). It was subsequently cloned into pPL451 to produce the plasmid pPL-Vpu (C).

Figure 2B:
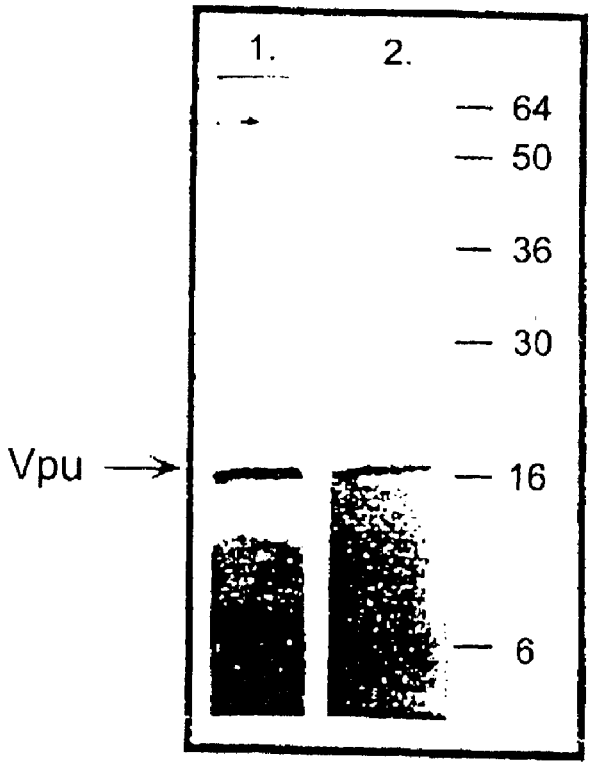

FIGS. 2A–2B Expression and purification of Vpu in E. coli. A. Western blotting after SDS-PAGE was used to detect expressed Vpu in E. coli extracts. Lanes 1–4 contain samples, at various stages of purity, of Vpu expressed from p2GEXVpu: lane 1, GST-Vpu fusion protein isolated by glutathione-agarose affinity chromatography; lane 2, Vpu liberated from the fusion protein by treatment with thrombin; lane 3, Vpu purified by HPLC anion exchange chromatography; lane 4, Vpu after passage through the immunoaffinity column. Lanes 5 and 6, membrane vesicles prepared from 42° C. induced cells containing pPL-Vpu or pPL451, respectively. B. Silver strained SDS-PAGE gel: lane 1, Vpu purified by HPLC anion exchange chromatography; lane 2, Vpu after passage through the immunoaffinity column.

Figure 3A:
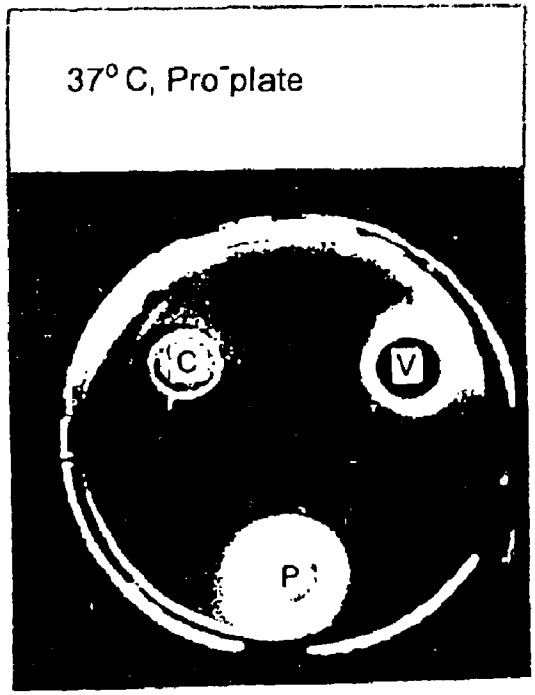
Figure 3B:
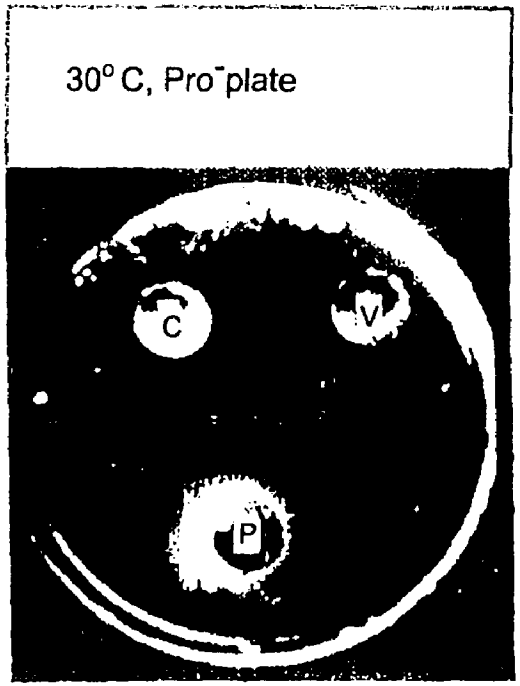
Figure 3C:
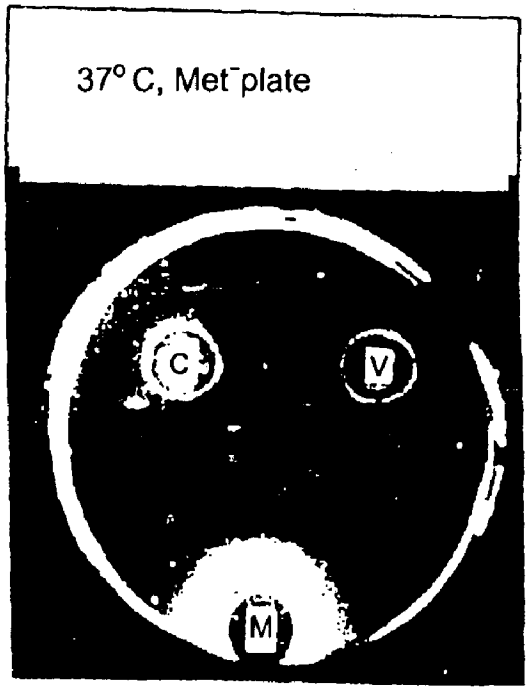
Figures 4A, 4B, 4C, 4D:
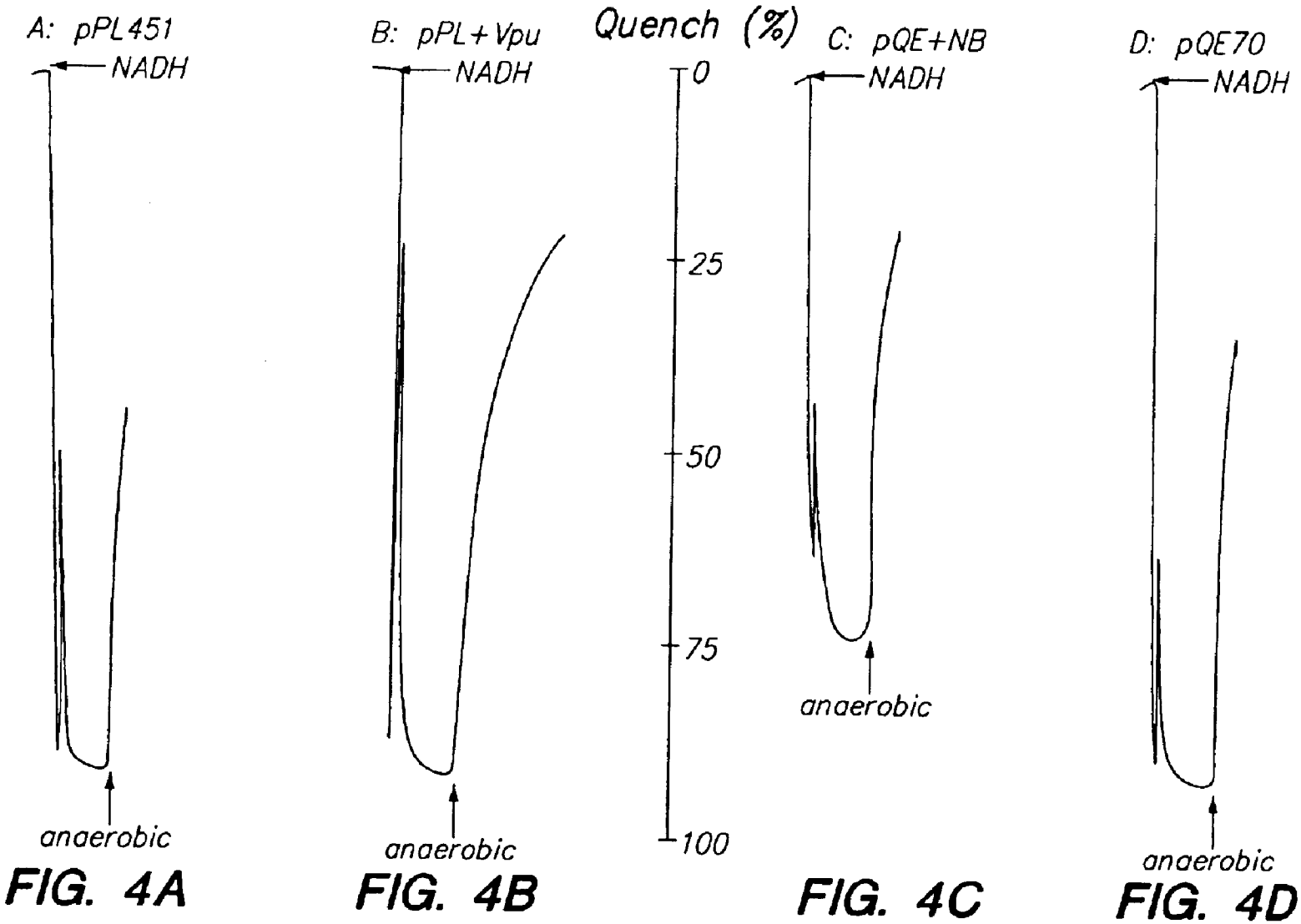

FIGS. 3A–3C Bacterial cross-feeding assays. A . full description of this assay is given in Example 1. For all plates, the Met−, Pro− auxotrophic strain was used to seed a soft agar overlay. Plates A and B contain minimal medium supplemented with methionine; in plate C the medium was supplemented with proline. To control for viability of the cells in the background lawn, the discs labelled P and M contained added proline or methionine, respectively. The discs labelled C and V were inoculated with Met+, Pro+ E. coli cells containing the plasmids pPL451 or pPL-Vpu, respectively. Plates were incubated at 37° C. (A and C) or 30° C.(B) for two days and photographed above a black background with peripheral illumination from a fluorescent light located below the plate. The images were recorded on a Novaline video gel documentation system. Light halos around the discs labelled P or M on all plates and around the disc labelled V on plate A indicate growth of the background lawn strain.

FIGS. 4A–4D NADH-dependent Atebrin fluorescence quenching from everted plasma membrane vesicles prepared from E. coli cells expressing Vpu (B) or the influenza B protein NB (C). Control vesicles were prepared from strains containing the appropriate expression vectors (A and D). NADH addition and the time at which the cuvette solution goes anaerobic are indicated by the arrows.

Figure 5A:
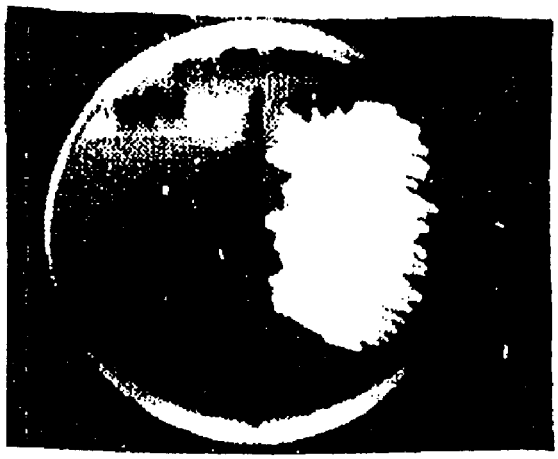
Figure 5B:
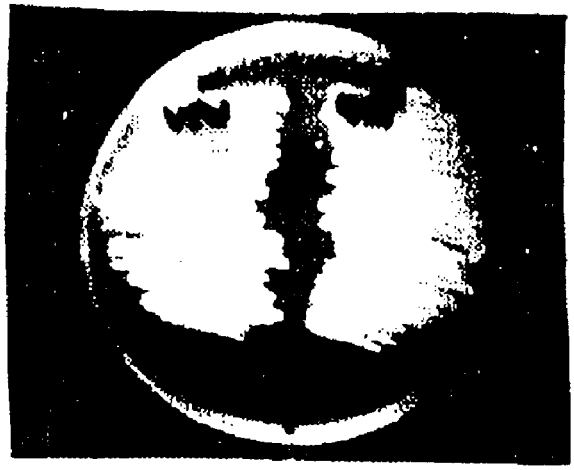

FIGS. 5A–5B The adenine growth-dependency assay. Expression of Vpu from the plasmic pPL-Vpu at 38° C. makes growth of the host E.coli cells dependent on the presence of adenine in the external media. Panel A: Minimal media agarose plate with E. coli cells containing pPL-Vpu streaked on the left hand side and cells containing pPL-451 (no Vpu gene) on the right hand side. Panel B: An identical plate and cell streaks, except that adenine (0.002% wt/v final) was added to the media before the plate was poured. Note that the Vpu expressing cells grow well when adenine is present in the plate.

Figure 6A:
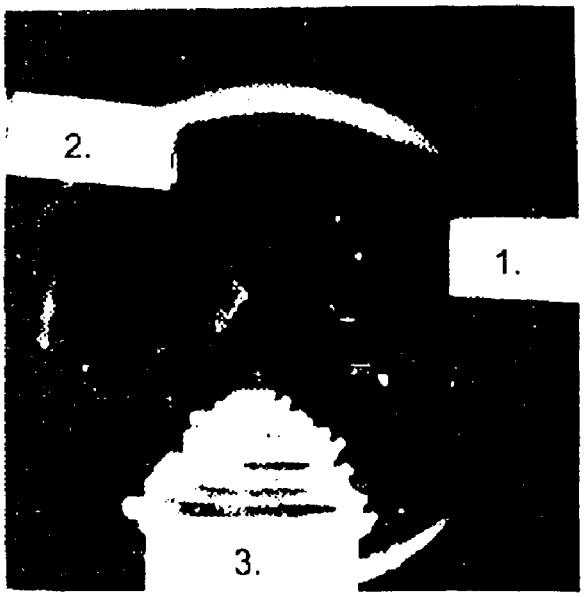
Figure 6B:
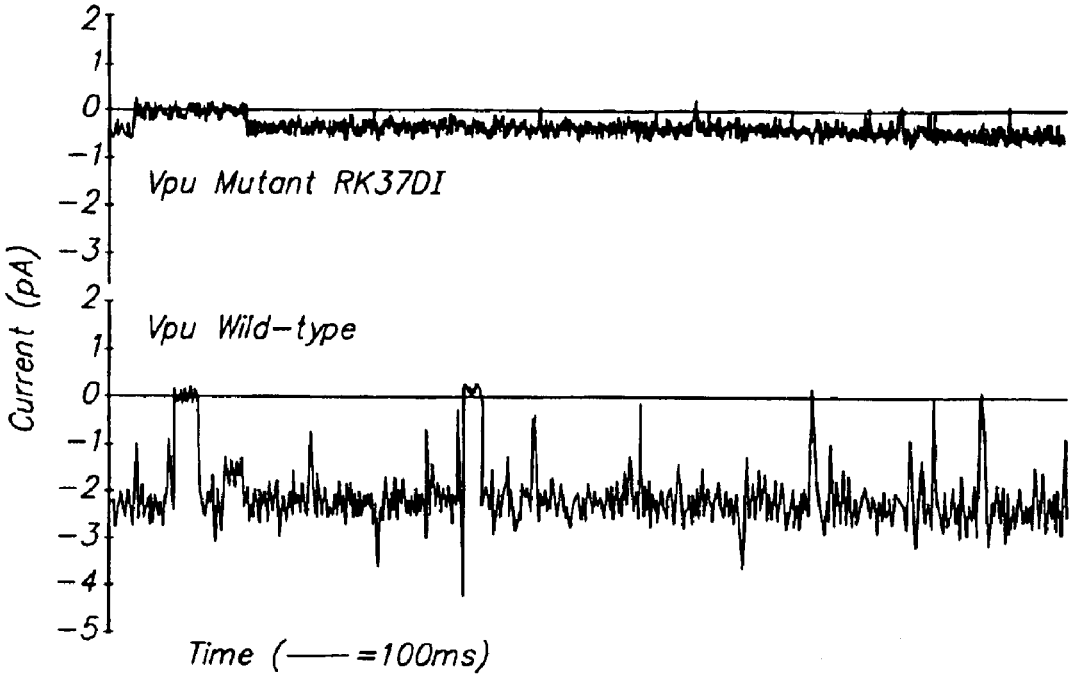

FIGS. 6A–6B Use of the adenine growth-dependence assay to detect mutant Vpu ion channels with altered channel activity. Panel A represents sections from a minimal medium agar plate (containing no adenine) onto which XL-1 Blue E.coli cells have been streaked containing either: 1., pPL-Vpu (expressing wild-type Vpu); 2., pPL-VpuRK37DI (expressing a mutant form of Vpu); or 3., pPL-451 (control plasmic with no Vpu gene). The plate was then incubated at 38° C. for two days. While the cells expressing wild-type Vpu did not grow (apart from a few revertant colonies), those expressing the Vpu mutant can clearly be seen to be growing, albeit not as efficiently as the no Vpu control cells.

When the RK37DI mutant Vpu protein was tested in the bilayer assay (Panel B) the channels were found to have a conductance of 3 picosiemens, which is approximately 20% of the wild-type channel conductance. The residual activity might explain why the cells containing the mutant plasmid did not grow as well as the no-Vpu control cells.

Figure 7B:
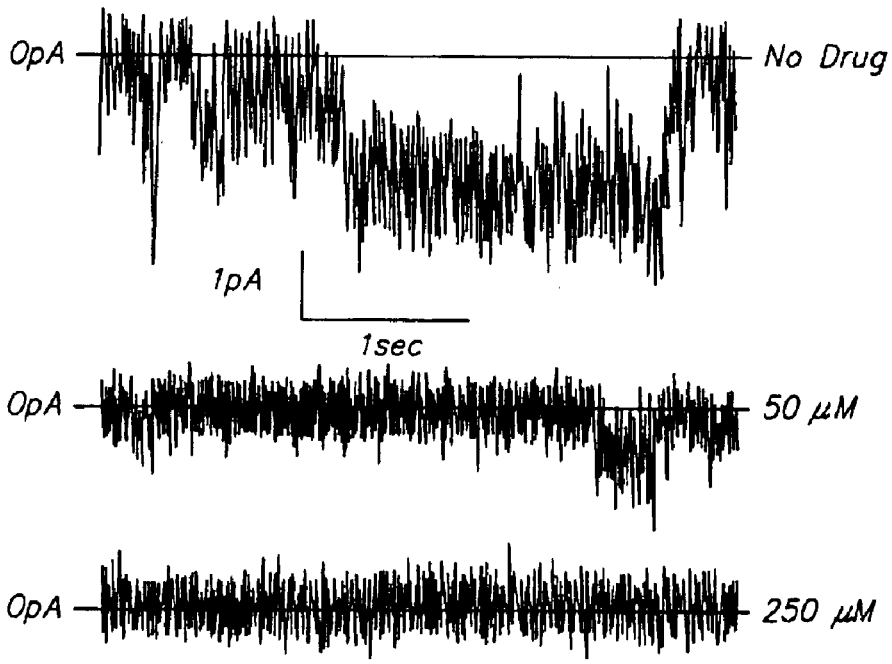
Figure 7A:
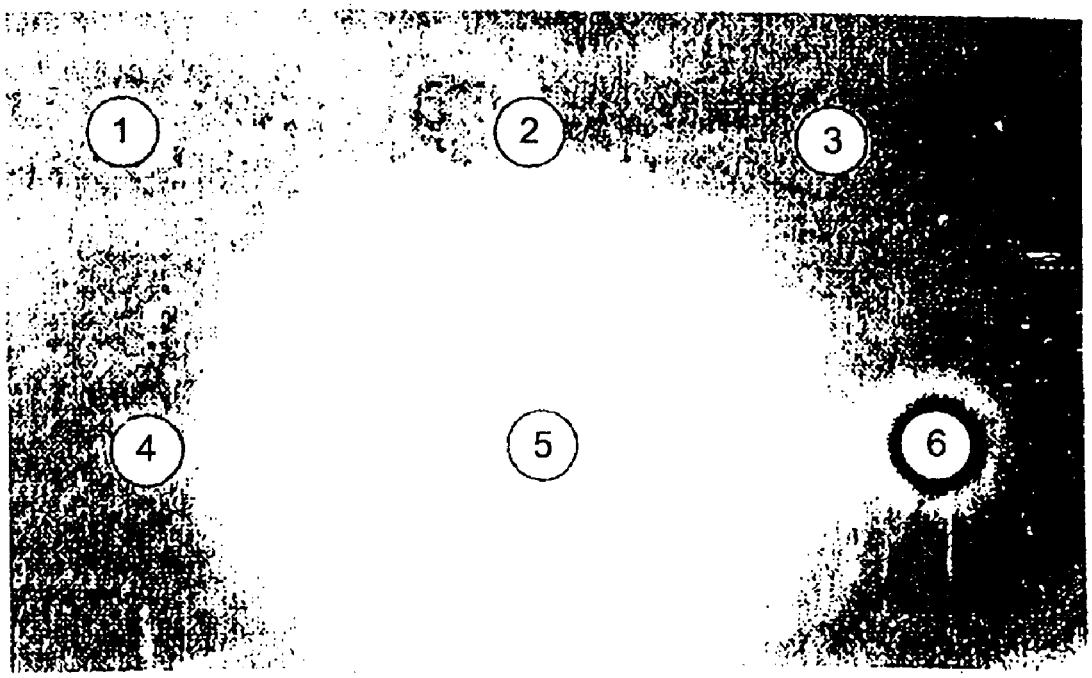

FIGS. 7A–7B Use of the adenine growth-dependence assay to screen for drugs which inhibit Vpu ion channel activity. Panel A represents a section from a minimal medium agar plate (containing no adenine) on to which a lawn of XL-1 Blue E. coli cells expressing wild-type Vpu (pPL-Vpu) has been seeded. At the numbered circles, 1 μl of a solution of various drugs has been applied to the plate and allowed to soak into the agar. The plate was then incubated at 38° C. for two days. At #'s 1–4 the drug has had no effect on Vpu's ability to prevent cell growth. At #5 a solution containing an excess of adenine was applied as a control—the bright ring around #5 indicates growing E.coli cells. At #6, compound ANU-9 was added—the faint but detectable ring of growth indicated a potential inhibition of Vpu channel activity by ANU-9. This was confirmed when ANU-9 was tested in the bilayer assay: Panel B shows partial inhibition of Vpu channel activity at 50 μM ANU-9 and complete inhibition at 250 μM.

EXAMPLE 1

This example demonstrates the functional expression of Vpu in E. coli host cells and the detection of changes in the permeability of the plasma-membrane of the host cells to proline by detecting leakage of proline from the host cells using the cross-feeding method. It will be understood that the same methods can be performed to demonstrate or determine the ion channel activity of peptides, polypeptides or protein other than Vpu.

Construction of recombinant plasmids p2GEXVpu and pPL-Vpu

The open reading frame encoding Vpu (SEQ ID No. 1—FIG. 1A) was amplified by PCR from a cDNA clone of an Nde1 fragment of the HIV-1 genome (isolate HXB2, a gift from Dr N. Deacon, McFarlane Burnet Centre, Melbourne, Australia). Native Pfu DNA polymerase (Stratagene; 0.035 U/μl) was chosen to catalyse the PCR reaction to minimise possible PCR introduced errors by virtue of the enzyme's proofreading activity. The 5', sense, primer (AGTAGGATCCATGCACCTATACC—SEQ ID No.2) introduces a BamH1 site (underlined) for cloning in-frame with the 3' end of the GST gene in p2GEX (1). This primer also repairs the start codon (bold T replaces a C) of the vpu gene which is a threonine codon in the HXB2 isolate. The 3', antisense, primer (TCTGGAATTCTACAGATCATCAAC—SEQ ID No. 3) introduces an EcoR1 site (underlined) to the other end of the PCR product to facilitate cloning. After 30 cycles of 94° C. for 45 sec, 55° C. for 1 min and 72° C. for 1 min in 0.5 ml thin-walled eppendorf tubes in a Perkin-Elmer thermocycler, the 268 bp fragment was purified, digested with BamH1 and EcoR1 and ligated to p2GEX prepared by digestion with the same two enzymes. The resultant recombinant plasmid p2GEXVpu, is illustrated in FIG. 1B. The entire Vpu open reading frame and the BamH1 and EcoR1 ligation sites were sequenced by cycle sequencing, using the Applied Biosystems dye-terminator kit, to confirm the DNA sequence.

To prepare the Vpu open reading frame for insertion into the pPL451 expression plasmid (2), p2GEXVpu was first digested with BamH1 and the 5' base overhang was filled in with Klenow DNA polymerase in the presence of dNTPs. The Vpu-encoding fragment was then liberated by digestion with EcoR1, purified from an agarose gel and ligated into pPL451 which had been digested with Hpa1 and EcoR1. Western blots subsequently confirmed that the pPL-Vpu construct (FIG. 1C) expressed Vpu after induction of cultures at 42° C. to inactivate the cI857 represser of the PR and PL promoters.

The pPL-Vpu construct was then inserted into E. coli host cells using known techniques (9).

Growth and expression characteristics of pPL-Vpu

On agar plates made from rich medium (e.g. Luria Broth supplemented with glucose), E. coli cells containing pPL-Vpu grew when incubated at 30° C. and 37° C. but not at 42° C., while control strains grew well at 42° C. Liquid cultures of cells containing pPL-Vpu were grown at 30° C. to OD600=0.84 then moved to grow at 42° C. for two hours (the final cell density was OD600=0.75) The plasma membrane fraction was prepared and western blotting detected a single band at approximately 16 kDa, indicating that Vpu was expressed and associated with the membranes (FIG. 2A, lane 5).

Cross-feeding experiments reveal that proline leaks out of cells expressing Vpu

Uptake of proline by E. coli is well characterised and active transport of the amino acid into the cells is known to use the sodium gradient as the energy source (3). It was predicted that if the sodium gradient were dissipated by a sodium channel in the plasma membrane than proline synthesised in the cytoplasm will diffuse out of the cells. To detect whether this proline leakage occurred, the following cross-feeding assay was used: A lawn of an E. coli strain auxotrophic for proline and methionine (Met− Pro−), was seeded and poured as a soft agar overlay on minimal media plates lacking proline but containing methionine. Sterile porous filter discs were inoculated with a Met+ Pro+ strain (XL-1 blue) containing either the pPL451 control plasmid or pPL-Vpu and placed onto the soft agar. The plates were then incubated at 37° C. or 30° C. for two days. After that time a halo of growth of the Met− Pro− strain was clearly visible surrounding the disc inoculated with the cells containing pPL-Vpu incubated at 37° C. (FIG. 3A). This growth can only be due to the leakage of proline from the Vpu-expressing cells on the disc. No such leakage was apparent from the control strain at 37° C. nor around either strain on plates grown at 30° C. (FIG. 3B).

Methionine does not leak out of cells expressing Vpu

In contrast to proline transport, the E. coli methionine permease is known to belong to the ABC transporter family (4) and hence be energised by ATP. Identical cross-feeding experiments to those described above were set up except that the Met− Pro− strain was spread on minimal plates lacking methionine but containing proline. No growth of this strain was evident around any of the discs (FIG. 3C), indicating that methionine was not leaking out of the XL-1 blue cells even when Vpu was being expressed.

Proton permeability of membrane vesicles is unaffected by the presence of Vpu

To investigate whether the Vpu sodium-conductive channel expressed in E. coli membranes was also permeable to H+, the NADH-dependent atebrin fluorescence quenching assay (5) was used. This technique can be used to measure the ability of E. coli membrane vesicles to maintain a proton gradient generated by the electron transport chain during oxidative phosphorylation. The fluorescent atebrin molecule contains two protonatable nitrogen atoms. The unprotonated form is electrically neutral and is able to equilibrate between the interior and exterior of the vesicles. The increased internal concentration of protons, generated in the presence of NADH ADP and oxygen, results in protonation of atebrin molecules that are inside the vesicles and the subsequent net accumulation of atebrin inside the vesicles results in quenching of its fluorescence. Vesicles leaky to protons, and hence unable to maintain a high H+in/H+out ratio, do not quench atebrin fluorescence as efficiently as control vesicles.

In this study, membrane vesicles prepared from E. coli cells expressing Vpu from pPL-Vpu were not more proton permeable than control vesicles prepared from the background strain (FIGS. 4, A and B). The Vpu protein was present in the membranes (see FIG. 2A, lanes 5 & 6) and it can therefore be concluded that it had not formed a channel permeable enough to protons to be detected by the fluorescence quenching technique.

The NB protein of influenza B has been shown to form cation-selective channels in bilayers (6) and may be equivalent to M2 of influenza A which has been shown to be a hydrogen ion channel (7). Membrane vesicles were prepared from a strain containing the plasmid pQE+NB. These vesicles contained the NB protein by western analysis (not shown) and had clearly reduced atebrin fluorescence quenching activity compared to the control strain (FIG. 4C and D), confirming that the NB channels are permeable to hydrogen ions. The fluorescence quenching technique is clearly capable of detecting the presence of proton-Vpu conducting channels and this control experiment provides support for the conclusion that the protein does not form a proton-conducting channel when expressed in E. coli.

EXAMPLE 2

This example demonstrates the functional expression of Vpu in E. coli cells and the detection of changes in the permeability of the plasma membrane of the host cell to adenine by detecting failure to thrive of the host cells when grown on minimal medium plates lacking adenine. As with Example 1, it will be understood that the same methods can be performed to demonstrate or determine the ion channel activity of peptides, polypeptides or proteins other than Vpu.

The same expression and control plasmids are used as described in Example 1 above (pPL-Vpu and pPL451, respectively). When cells of the E. coli strain XL-1 Blue containing the Vpu expression plasmid pPLVpu are incubated at 37° C. on minimal medium plates the host cells fail to grow (FIG. 5). Because of an undefined temperature sensitive mutation in the adenine biosynthesis pathway of E. coli strain XL-1 Blue, this strain is unable to up-regulate adenine biosynthesis in response to adenine leakage induced as a result of Vpu sodium channel expression. Growth of these Vpu-expressing cells can be restored if adenine is included in the nutrient medium at sufficiently high concentration to negate the net driving force for loss of this molecule from the cells.

In contrast, the same host cells containing the control plasmid pPL451 (which is identical to pPL-Vpu except for the absence of the DNA segment encoding the Vpu protein), grow normally at 37° C. on minimal medium plates in the absence (or presence) of adenine (FIG. 5).

These observations indicate that expression of Vpu in the XL-1 Blue cells has caused leakage of adenine from the cells in a manner analogous to the proline leakage described in Example 1. In this case, the test for a functioning sodium channel expressed in the E. coli plasma membrane is the inability of the host cells to grow in the absence of adenine.

EXAMPLE 3

This example demonstrates the use of the adenine growth-dependence assay to detect mutant forms of the Vpu protein affecting channel activity.

A site directed mutation was introduced to the Vpu gene so as to change the amino acids Arg and Lys as positions 37 and 38 to Glu and Ile in the protein expressed from the mutated gene (called "RK37DI mutant Vpu"). In electrophysiological assay of channel function this mutation was shown to reduce the conductance of the ion channels formed to approx 20% of that of the wild-type channels (3 picosiemens versus 15 picosiemens, respectively). FIG. 6B shows a comparison of the size of the currents produced by mutant and wild-type channels in planar lipid bilayers.

On minimal media plates (containing no adenine—as per FIG. 5), cells containing the plasmid encoding the RK37DI mutant Vpu had a partial growth phenotype compared to cells containing the wild-type Vpu gene (which don't grow at all) and to cells containing no Vpu gene (in which growth is unaffected)—See FIG. 6.

This result illustrates the correlation between the biological (adenine growth dependence) assay and the in-vitro (electrophysiological) assay in terms of their abilities to reflect Vpu channel activities.

EXAMPLE 4

This example demonstrates the screening method of the present invention for screening test substances for ion channel inhibitory properties using the methods of Examples 1 and 2 to obtain functional expression of Vpu in E. coli host cells and detecting leakage of proline or adenine from the host cells using the cross-feeding method.

For cases in which the cross-feeding method is being employed to detect the channel activity (as in Example 1), filter discs inoculated with the channel-expressing host cells are subjected to addition of small volumes of solution containing the substance(s) to be tested. If the added drug inhibits channel activity, then cross-feeding of the background strain is not observed.

For cases in which adenine requirement for growth is being employed to detect the channel activity (as in Example 2), the XL-1 Blue host cells expressing the channel protein are spread to form a lawn of cells on minimal medium plates lacking adenine. The test substance(s) is then applied to defined areas of the plates and growth of the XL-1 Blue cells around the area in which the test substance(s) is applied indicates channel inhibition has occurred to prevent adenine leakage (FIG. 7A).

As an example, a compound (ANU-9) has been identified which, when added at a discrete location to such a minimal medium plate (no adenine) as described above, allows E. coli cells expressing Vpu to grow in a region surrounding the point of application (FIG. 7A). This indicates that in the region of growth compound ANU-9 is at a concentration sufficient to inhibit the Vpu ion channel such that cell growth can occur in the absence of adenine.

ANU-9 was subsequently screened in the electrophysiological assay for its ability to block Vpu ion channel activity (FIG. 7B). At 50 μM channels were severely inhibited, with only infrequent, small openings detected (middle trace FIG. 7B), while at 250 μM channel activity was completely inhibited (lower trace FIG. 7B).

Detection of ion channel modulating activity of a test substance

A lawn of an E. coli strain auxotrophic for proline and methionine (Met− Pro−), is seeded and poured at a soft agar overlay on minimal media plates lacking proline but containing methionine. Sterile porous filter discs are impregnated with a test substance to be screened and inoculated with a Met+ Pro+ strain (XL-1 blue) containing the pPL-Vpu construct (prepared as described in Example 1) and placed onto the soft agar. The plates are then incubated at 37° C. or 30° C. for two days. After that time a halo of growth of the Met− Pro− strain is clearly visible surrounding the disc inoculated with the cells containing pPL-Vpu if the test substance is one that does not block the Vpu ion channel. If the test substance is one that does block the Vpu ion channel, no growth of the Met− Pro− strain is observed around the disc. A control experiment is performed whereby a disc impregnated with the test substance is used to show that the test substance has no effect on the normal growth of E. coli.

Persons skilled in this art will appreciate that variations and modifications may be made to the invention as broadly described herein, other than those specifically described without departing from the spirit and scope of the invention. It is to be understood that this invention extends to include all such variations and modifications.

REFERENCES

1. Piller S c, Ewart G D, Premkumar A, Cox G B, and Gage P W, (1996), Vpr protein of human immunodeficiency virus type 1 forms cation-selective channels in planar lipid bilayers, Proceedings of the National Academy of Sciences of the United States of America 93:111–115.
2. Love C A, Lilley P E, and Dixon N E, (1996), Stable high-copy number bacteriophage lambda promoter vectors for overproduction of proteins in Escherichia coli. Gene. 176:49–53.
3. Yamato I, Kotani M, Oka Y, and Anraku Y, (1994), Site-specific alteration of arginine 376) the unique positively charged amino acid residue in the mid-membrane-spanning reginos of the proline carrier of Escherichia coli. Journal of Biological Chemistry, 269:5729–5724.
4. Rosen B R, ATP-coupled solute transport systems, in Escherichia coli and Salmonella typhimurium: Cellular and molecular biology, F. C. Neidhardt, Editor. 1987, American Society for Microbiology: Washington D.C., p. 760–767.
5. Haddock B A and Downie J A, (1974), The reconstitution of functional respiratory chains in membranes from electron-transport-deficient mutants of Escherichia coli as demonstrates by quenching of atebrin fluorescence. Biochem. J. 142:703–706.
6. Sunstrom N A, Premkumar L S, Premkumar A, Ewart G and Cox G B, (1996), Ion channels formed by N B, and influenze B virus protein. Journal of Membrane Biology 150:127–132.
7. Schroeder C, Ford C M, Wharton S A, and Hay A J, (1994), Functional reconstitution in lipid vesicles of influenza virus M2 protein expressed by baculovirus: evidence for proton transfer activity, J. Gen Virol. 75:3477–3484.
8. Ewart G D, Sutherland T, Gage P W, and Cox G B, (1996). The Vpu protein of HIV-1 forms cation selective ion channels. J. Virol. 70:7108–7115.
9. Sambrook J, Fritsch E F, and Maniatis T, (1989). Molecular Cloning: A Laboratory Manual, 2nd Ed. Cold Spring Harbor Laboratory, Cold Spring Harbor, N.Y.

SEQUENCE LISTING

```
<160> NUMBER OF SEQ ID NOS: 3

<210> SEQ ID NO 1
<211> LENGTH: 82
<212> TYPE: PRT
<213> ORGANISM: HIV-1

<400> SEQUENCE: 1

Met Gln Pro Ile Pro Ile Val Ala Ile Val Ala Leu Val Val Ala Ile
  1               5                  10                  15

Ile Ile Ala Ile Val Val Trp Ser Ile Val Ile Ile Glu Tyr Arg Lys
             20                  25                  30

Ile Leu Arg Gln Arg Lys Ile Asp Arg Leu Ile Asp Arg Leu Ile Glu
         35                  40                  45

Arg Ala Glu Asp Ser Gly Asn Glu Ser Glu Gly Glu Ile Ser Ala Leu
     50                  55                  60

Val Glu Met Gly Val Glu Met Gly His His Ala Pro Trp Asp Val Asp
 65                  70                  75                  80

Asp Leu


<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:5' sense
```

-continued

```
      primer

<400> SEQUENCE: 2

agtaggatcc atgcaaccta tacc                                          24


<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:3' antisense

<400> SEQUENCE: 3

tctggaattc tacagatcat caac                                          24
```

We claim:

1. A screening method for determining ion channel modulating activity of a test substance having potential for such modulating activity, which comprises the steps of:

(i) *contacting a host cell with the test substance, said host cell* expressing a peptide, polypeptide or protein in the plasma membrane [of a host cell], said peptide, polypeptide or protein having ion channel activity when expressed as a heterologous protein in the plasma membrane of the host cell; *and*

[(ii) contacting said host cell with the test substance; and]

[(iii)] (*ii*) determining changes to the ion channel activity of said heterologous protein induced by the test substance, wherein the changes to the ion channel activity of the heterologous protein induced by the test substance are determined by detecting the effect of the test substance on changes in net movement across the plasma membrane of the host cell of small cellular metabolite molecules which do not directly permeate the ion channel formed by said heterologous protein.

2. A method according to claim 1, wherein the effect of the test substance on changes in the net movement of proline or adenine molecules across the plasma membrane is detected.

3. A method according to claim 1, wherein said host cell is E. coli.

4. A method according to claim 1, wherein said substance having ion channel activity is a heterologous cation channel protein.

5. A method according to claim 4, wherein said substance having ion channel activity is a heterologous sodium channel protein.

6. A method according to claim 4, wherein said substance having ion channel activity is the HIV-1 Vpu integral membrane protein.

7. A method according to claim 1, wherein leakage of said small cellular metabolite molecules from the host cell is detected.

8. A method according to claim 7, wherein leakage of said small cellular metabolite molecules from the host cells is detected by either:

(i) cross-feeding of cells which are auxotrophic for the leaked metabolite; or (ii) failure of cells expressing the ion channel to grow in the absence of the leaking metabolite being supplied in the external medium.

[9. A method for determining ion channel modulating activity of a test substance having potential for such modulating activity, which comprises the steps of:

(i) expressing a peptide, polypeptide or protein in the plasma membrane of a host cell, said peptide, polypeptide or protein having ion channel activity when expressed as a heterologous protein in the plasma membrane of the host cell;

(ii) contacting said host cell with the test substance; and (iii) determining changes to the ion channel activity of said heterologous protein induced by the test substance, wherein the changes to the ion channel activity of the heterologous protein induced by the test substance are determined by detecting the effect of the test substance on changes in permeability of the plasma membrane of the host cell to small cellular metabolite molecules, wherein said heterologous protein having ion channel activity is the HIV-1 Vpu integral membrane protein.]

10. [The method of claim 9] *A screening method for determining ion channel modulating activity of a test substance having potential for such modulating activity, which comprises the steps of:*

(*i*) *contacting a host cell with the test substance, said host cell expressing a peptide, polypeptide or protein in the plasma membrane, said peptide, polypeptide or protein having ion channel activity when expressed as a heterologous protein in the plasma membrane of the host cell; and*

(*ii*) *determining changes to the ion channel activity of said heterologous protein induced by the test substance, wherein the changes to the ion channel activity of the heterologous protein induced by the test substance are determined by detecting the effect of the test substance on changes in permeability of the plasma membrane of the host cell to small cellular metabolite molecules, wherein said heterologous protein having ion channel activity is the HIV-1 Vpu integral membrane protein,* wherein the effect of the test substance on changes in the permeability of the plasma membrane to proline or adenine molecules is detected.

[11. The method of claim 9 wherein said host cell is E. coli.]

[12. The method of claim 9 wherein leakage of metabolite from the host cell is detected.]

[13. The method of claim 12 wherein leakage of metabolite from the host cells is detected by either:

(i) cross-feeding of cells which are auxotrophic for the leaked metabolite; or (ii) failure of cells expressing the ion channel to grow in the absence of the leaking metabolite being supplied in the external medium.]

[14. A screening method for determining ion channel modulating activity of a test substance having potential for such modulating activity, which comprises the steps of:

(i) expressing HIV-1 Vpu integral membrane protein in the plasma membrane of a host cell, said protein having ion channel activity when expressed as a heterologous protein in the plasma membrane of the host cell;

(ii) contacting said host cell with the test substance; and (iii) determining changes to the ion channel activity of said heterologous protein induced by the test substance, wherein the changes to the ion channel activity of the heterologous protein induced by the test substance are determined by detecting the effect of the test substance on changes in net movement across the plasma membrane of the host cell of small cellular metabolite molecules.]

15. [The method of claim 14] *A screening method for determining ion channel modulating activity of a test substance having potential for such modulating activity, which comprises the steps of:*

(*i*) *contacting a host cell with the test substance, said host cell expressing HIV-1 Vpu integral membrane protein in the plasma membrane, said protein having ion channel activity when expressed as a heterologous protein in the plasma membrane of the host cell; and*

(*ii*) *determining changes to the ion channel activity of said heterologous protein induced by the test substance, wherein the changes to the ion channel activity of the heterologous protein induced by the test substance are determined by detecting the effect of the test substance on changes in net movement across the plasma membrane of the host cell of small cellular metabolite molecules,* wherein the effect of the test substance on changes in the movement of proline or adenine molecules is detected.

[16. The method of claim 14 wherein said host cell is E. coli.]

[17. The method of claim 14 wherein leakage of metabolite from the host cell is detected.]

[18. The method of claim 17 wherein leakage of metabolite from the host cells is detected by either:

(i) cross-feeding of cells which are auxotrophic for the leaked metabolite; or (ii) failure of cells expressing the ion channel to grow in the absence of the leaking metabolite being supplied in the external medium.]

[19. A screening method for determining ion channel modulating activity of a test substance having potential for such modulating activity, which comprises the steps of:

(i) expressing HIV-1 Vpu integral membrane protein in the plasma membrane of a host cell, said protein having ion channel activity when expressed as a heterologous protein in the plasma membrane of the host cell;

(ii) contacting said host cell with the test substance; and (iii) determining changes to the ion channel activity of said heterologous protein induced by the test substance.]

20. [The method of claim 19] *A screening method for determining ion channel modulating activity of a test substance having potential for such modulating activity, which comprises the steps of:*

(*i*) *contacting a host cell with the test substance, said host cell expressing HIV-1 Vpu integral membrane protein in the plasma membrane, said protein having ion channel activity when expressed as a heterologous protein in the plasma membrane of the host cell; and*

(*ii*) *determining changes to the ion channel activity of said heterologous protein induced by the test substance,* wherein the effect of the test substance on changes in the permeability of the plasma membrane to proline or adenine molecules is detected.

[21. The method of claim 19 wherein said host cell is E. coli.]

[22. The method of claim 19 wherein leakage of metabolite from the host cell is detected.]

[23. The method of claim 22 wherein leakage of metabolite from the host cells is detected by either:

(i) cross-feeding of cells which are auxotrophic for the leaked metabolite; or (ii) failure of cells expressing the ion channel to grow in the absence of the leaking metabolite being supplied in the external medium.]

* * * * *